(12) United States Patent
Kolouri et al.

(10) Patent No.: US 11,791,018 B1
(45) Date of Patent: Oct. 17, 2023

(54) SYSTEM AND METHOD FOR DISCOVERING CHEMICALLY ACTIVE COMPOUNDS OF A MOLECULE

(71) Applicant: HRL Laboratories, LLC, Malibu, CA (US)

(72) Inventors: Soheil Kolouri, Agoura Hills, CA (US); Phillip E. Pope, Homosassa, FL (US); Mohammad Rostami, Santa Monica, CA (US); Charles E. Martin, Santa Monica, CA (US); Heiko Hoffmann, Simi Valley, CA (US)

(73) Assignee: HRL LABORATORIES, LLC, Malibu, CA (US)

( * ) Notice: Subject to any disclaimer, the term of this patent is extended or adjusted under 35 U.S.C. 154(b) by 1,115 days.

(21) Appl. No.: 16/513,592

(22) Filed: Jul. 16, 2019

Related U.S. Application Data

(60) Provisional application No. 62/711,857, filed on Jul. 30, 2018.

(51) Int. Cl.
| | |
|---|---|
| *G16C 20/10* | (2019.01) |
| *G16C 20/20* | (2019.01) |
| *G16C 20/80* | (2019.01) |
| *G16C 20/50* | (2019.01) |
| *G06N 3/08* | (2023.01) |
| *G16C 20/70* | (2019.01) |

(52) U.S. Cl.
CPC ............... *G16C 20/10* (2019.02); *G06N 3/08* (2013.01); *G16C 20/20* (2019.02); *G16C 20/50* (2019.02); *G16C 20/70* (2019.02); *G16C 20/80* (2019.02)

(58) Field of Classification Search
CPC .......... G16C 20/20; G16C 20/10; G16C 20/80
See application file for complete search history.

(56) References Cited

OTHER PUBLICATIONS

Junqi Li, Steven G. Ballmer, Eric P. Gillis, Seiko Fujii, Michael J. Schmidt, Andrea M. E. Palazzolo, Jonathan W. Lehmann, Greg F. Morehouse, Martin D. Burke. "Synthesis of many different types of organic small molecules using one automated process." Science Volume 347, Issue 6227, Mar. 13, 2015, pages 1221 - 1226.

Kipf, Thomas N., and Max Welling. "Variational graph auto-encoders." arXiv preprint arXiv:1611.07308, pages 1-3, 2016.

Trobe, M. and Burke, MD. "The Molecular Industrial Revolution: Automated Synthesis of Small Molecules." Agnew Chem Int Ed Engl., 57(16): pages 4192-4214, 2018.

(Continued)

*Primary Examiner* — Lam S Nguyen
(74) *Attorney, Agent, or Firm* — TOPE-MCKAY & ASSOCIATES

(57) ABSTRACT

Described is a system for automatically identifying chemical properties of a molecule. A chemical representation of a molecular structure is converted into atomic features and an adjacency matrix. The atomic features and the adjacency matrix are processed with a neural network, resulting in neural activations corresponding to each atom in the molecular structure. The system determines a probability for each atom quantifying its relevance for a given chemical characteristic. The probabilities are displayed as a graphical representation on the molecular structure, and groups of atoms are identified for the given chemical characteristic from the graphical representation. The identified groups of atoms for the given chemical characteristic are stored in a database, and a new molecule having the given chemical characteristic is designed based on the stored identified groups of atoms.

12 Claims, 12 Drawing Sheets

GCNN architecture in Module 2  310

Softmax classification  708
Average pooling  706
$l = 2$  704
$l = 1$  702
$l = 0$  700

Graph convolutional layer-wise propagations:

$$X^{(l+1)} = \sigma(\tilde{D}^{-\frac{1}{2}} \tilde{A} \tilde{D}^{-\frac{1}{2}} X^{(l)} W^{(l)})$$

Where $X^{(l)}$ represents the features at layer $l$, and $W^{(l)} \in \mathbb{R}^{d_l \times d_{l+1}}$ are the weights at later $l$.

(56) References Cited

OTHER PUBLICATIONS

Weininger D. "SMILES, a chemical language and information system. 1. Introduction to methodology and encoding rules" Journal of Chemical Information and Modeling. 28 (1): pages 31-36, 1988.
Wu, Z. et al. "MoleculeNet: a benchmark for molecular machine learning." Chemical science 9.2 (2018): pages 513-530.
Xue, Y. et al. "Phase-Mapper: An AI Platform to Accelerate High Throughput Materials Discovery." Proc. Of the 29th AAAI Conf. on Innovative Applications (IAAI-17), pages 4635-4642, 2017.
Zimmerman, J. and Anastas, P. "Toward designing safer chemicals." Science, Vol. 347, Issue 6219, page 215, 2015.

SYSTEM AND METHOD FOR DISCOVERING CHEMICALLY ACTIVE COMPOUNDS OF A MOLECULE

CROSS-REFERENCE TO RELATED APPLICATIONS

This is a Non-Provisional Application of U.S. Provisional Application No. 62/711,857, filed in the United States on Jul. 30, 2018, entitled, "Method for Discovering Chemically Active Compounds of a Molecule," the entirety of which is incorporated herein by reference.

BACKGROUND OF INVENTION

Field of Invention

The present invention relates to a system for automatically identifying chemical properties of a molecule and, more particularly, to a system for automatically identifying chemical properties of a molecule and localizing the molecular compounds that contribute to the identified properties.

Description of Related Art

Recent research efforts in machine learning on molecular structures have focused on four fields: quantum mechanics, where the interest is in prediction of electronic properties of molecules (e.g., atomization energy, excited state energy, etc.); physical chemistry, where the interest is in predicting solubility of molecules and such; 3) biophysics, where the interest is in predicting the effect of certain molecules on specific diseases (e.g., inhibition of HIV); and 4) physiology, where the interest is on predicting the chemical effect of a molecule on certain organ classes (e.g., blood-brain barrier penetration, drug toxicity, etc.).

The majority of existing efforts are only interested in predicting certain chemical characteristics of an input molecule. For instance, prior works on predictive modeling that use the physicochemical properties and structural motifs of a chemical to reduce hazards (e.g., toxicity) through molecular design have relied on detailed knowledge and models about the human body's absorption, distribution, metabolism, and excretion of chemicals (see Literature Reference No. 4 of the List of Incorporated Literature References).

Another branch of work focuses on using machine learning to accelerate human designed and executed experiments for materials design. For example, Literature Reference No. 5 discloses a new method proposed to automatically identify distinct x-ray diffraction patterns that are indicative of unique materials, which is normally done by hand.

Thus, a continuing need exists for a system that not only predicts the chemical characteristics of an input molecule without a priori knowledge, but also automatically identifies the compounds that contribute to these characteristics, providing a guideline for scientists in the design process.

SUMMARY OF INVENTION

The present invention relates to a system for automatically identifying chemical properties of a molecule and, more particularly, to a system for automatically identifying chemical properties of a molecule and localizing the molecular compounds that contribute to the identified properties. The system comprises one or more processors and a non-transitory computer-readable medium having executable instructions encoded thereon such that when executed, the one or more processors perform multiple operations. The system converts a chemical representation of a molecular structure into atomic features and at least one adjacency matrix. The atomic features and the at least one adjacency matrix are processed with a neural network, resulting in neural activations corresponding to each atom in the molecular structure. A probability is determined for each atom quantifying its relevance for a given chemical characteristic. The probabilities are displayed as a graphical representation on the molecular structure, and groups of atoms are identified for the given chemical characteristic from the graphical representation. The identified groups of atoms for the given chemical characteristic are stored in a database, and a new molecule having the given chemical characteristic is designed based on the stored identified groups of atoms.

In another aspect, the system causes a molecule synthesizer to synthesize the new molecule.

In another aspect, a chemical characteristic of an input molecular structure is predicted without a priori knowledge.

In another aspect, in converting the chemical representation, the system generates a d-dimensional atomic feature for each atom, resulting in a $N \times d$ matrix, where N denotes a number of atoms in the molecular structure. An adjacency matrix A is generated representing chemical bonds between atoms, wherein the adjacency matrix A is a binary matrix, with elements $A_{i,j}$ indicating whether node i and node j are connected via a chemical bond.

In another aspect, the neural network is a graph-convolutional neural network (GCNN) comprising a plurality of layers, and where in processing the atomic features and the at least one adjacency matrix, the one or more processors further perform an operation of propagating the atomic features at each layer according to the following:

$$X^{(l+1)} = \sigma\left(\tilde{D}^{-\frac{1}{2}}\tilde{A}\tilde{D}^{-\frac{1}{2}}X^{(l)}W^{(l)}\right),$$

where $$\tilde{A} = A + I, \tilde{D}_{ii} = \Sigma_j \tilde{A}_{ij} \text{ and } \tilde{D}_{ij} = 0$$

for $i \neq j$, I represents an identity matrix of the same size as A, l represents a convolutional layer, $X^{(l)}$ represents the atomic features at layer l, $W^{(l)}$ represents neural weights, and $\sigma(\cdot)$ is a nonlinear function used in the GCNN.

In another aspect, the neural network is trained to obtain parameters $W^{(l)}$, for $l = 1, ..., L$ and $\omega_j$ for $j = 0, ..., d_L$, where L represents a total number of convolutional layers, where $\omega_j$ represents a softmax classifier parameter, and wherein a mean squared error loss function is minimized as follows:

$$argmin_{W^{(l)}, \omega} \Sigma_k \left\| \frac{1}{N} \Sigma_{n=1}^{N} \underbrace{\left(\Sigma_{j=1}^{d_L} \omega_j \left(X^k\right)_{n,j}^{(L)} + \omega_0\right)}_{\hat{x}_n} - y^k \right\|_2^2,$$

where $(X^k)^{(0)}$ represents atomic features from a k'th molecular structure in a training set, $d_L$ is a dimension of the atomic feature in the $L^{th}$ layer, $y^k$ is a ground-truth chemical characteristic, and $(X^k)^{(l+1)} =$ $$\sigma\left((\tilde{D}^k)^{-\frac{1}{2}}(\tilde{A}^k)(\tilde{D}^k)^{-\frac{1}{2}}(X^k)^{(l)}W^{(l)}\right).$$

Finally, the present invention also includes a computer program product and a computer implemented method. The computer program product includes computer-readable instructions stored on a non-transitory computer-readable medium that are executable by a computer having one or more processors, such that upon execution of the instructions, the one or more processors perform the operations listed herein. Alternatively, the computer implemented method includes an act of causing a computer to execute such instructions and perform the resulting operations.

BRIEF DESCRIPTION OF THE DRAWINGS

The objects, features and advantages of the present invention will be apparent from the following detailed descriptions of the various aspects of the invention in conjunction with reference to the following drawings, where.

DETAILED DESCRIPTION

Figure 1:
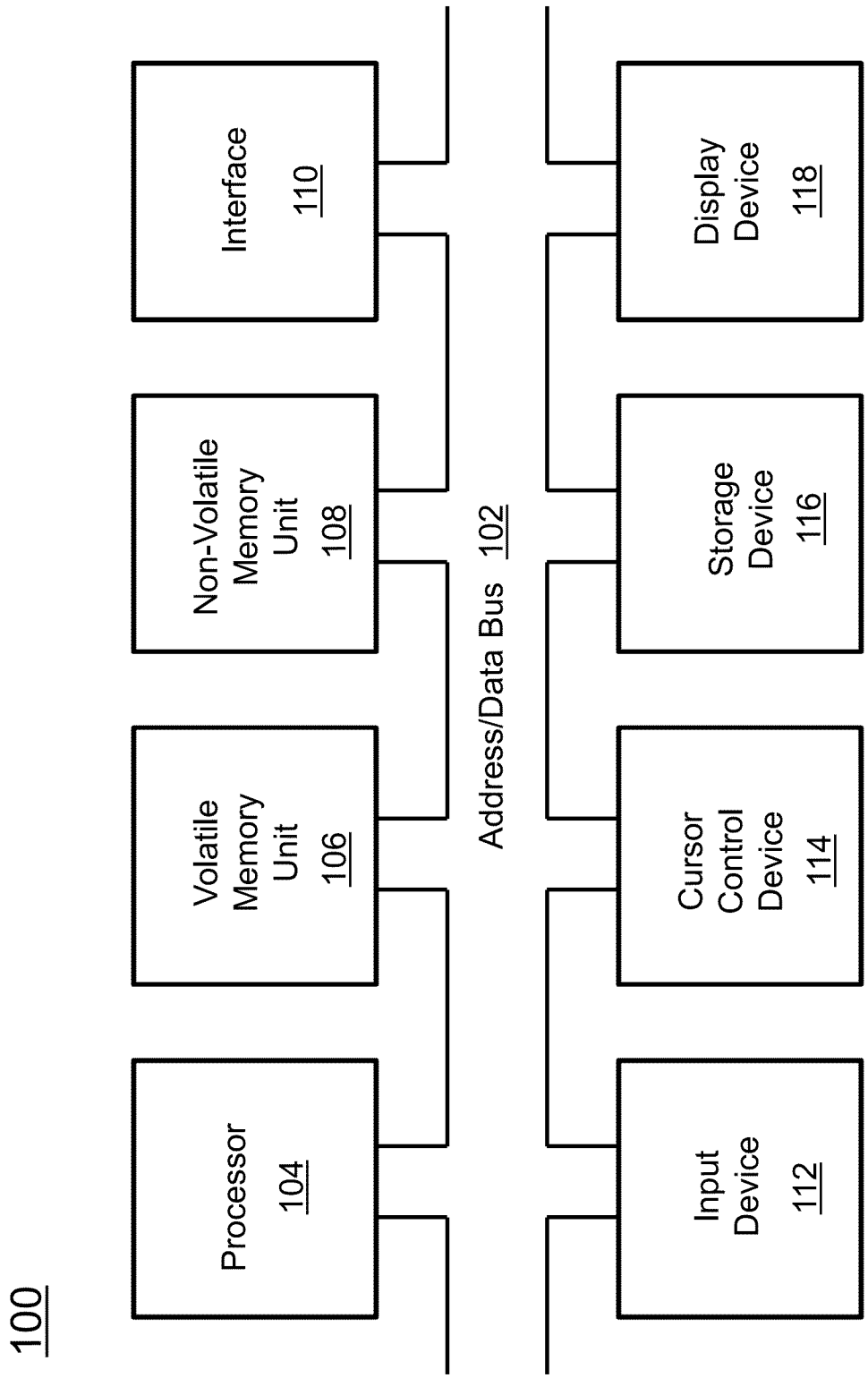
FIG. 1 is a block diagram depicting the components of a system for automatically identifying chemical properties of a molecule according to some embodiments of the present disclosure.

The present invention relates to a system for automatically identifying chemical properties of a molecule and, more particularly, to a system for automatically identifying chemical properties of a molecule and localizing the molecular compounds that contribute to the identified properties. The following description is presented to enable one of ordinary skill in the art to make and use the invention and to incorporate it in the context of particular applications. Various modifications, as well as a variety of uses in different applications will be readily apparent to those skilled in the art, and the general principles defined herein may be applied to a wide range of aspects. Thus, the present invention is not intended to be limited to the aspects presented, but is to be accorded the widest scope consistent with the principles and novel features disclosed herein.

In the following detailed description, numerous specific details are set forth in order to provide a more thorough understanding of the present invention. However, it will be apparent to one skilled in the art that the present invention may be practiced without necessarily being limited to these specific details. In other instances, well-known structures and devices are shown in block diagram form, rather than in detail, in order to avoid obscuring the present invention.

The reader's attention is directed to all papers and documents which are filed concurrently with this specification and which are open to public inspection with this specification, and the contents of all such papers and documents are incorporated herein by reference. All the features disclosed in this specification, (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

Furthermore, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of" or "act of" in the claims herein is not intended to invoke the provisions of 35 U.S.C. 112, Paragraph 6.

Before describing the invention in detail, first a list of cited references is provided. Next, a description of the various principal aspects of the present invention is provided. Finally, specific details of various embodiment of the present invention are provided to give an understanding of the specific aspects.

List of Incorporated Literature References

The following references are cited and incorporated throughout this application. For clarity and convenience, the references are listed herein as a central resource for the reader. The following references are hereby incorporated by reference as though fully set forth herein. The references are cited in the application by referring to the corresponding literature reference number, as follows:

1. Weininger D. "SMILES, a chemical language and information system. 1. Introduction to methodology and encoding rules". Journal of Chemical Information and Modeling. 28 (1): 31-6, 1988.
2. Kipf, Thomas N., and Max Welling. "Variational graph auto-encoders." arXiv preprint arXiv:1611.07308, 2016.
3. Junqi Li, Steven G. Ballmer, Eric P. Gillis, Seiko Fujii, Michael J. Schmidt, Andrea M. E. Palazzolo, Jonathan W. Lehmann, Greg F. Morehouse, Martin D. Burke. "Synthesis of many different types of organic small molecules using one automated process." Science Volume 347, Issue 6227, 13 Mar. 2015, Pages 1221 – 1226.
4. Zimmerman, J. and Anastas, P. "Toward designing safer chemicals." Science, Vol. 347, Issue 6219, 215, 2015.
5. Xue, Y. et al. "Phase-Mapper: An AI Platform to Accelerate High Throughput Materials Discovery." Proc. Of 6. Wu, Z. et al. "MoleculeNet: a benchmark for molecular machine learning." Chemical science 9.2 (2018): 513-530.
7. Trobe, M. and Burke, MD. "The Molecular Industrial Revolution: Automated Synthesis of Small Molecules." Agnew Chem Int Ed Engl., 57(16): 4192-4214, 2018.

Principal Aspects

Various embodiments of the invention include three "principal" aspects. The first is a system for automatically identifying chemical properties of a molecule. The system is typically in the form of a computer system operating software or in the form of a "hard-coded" instruction set. This system may be incorporated into a wide variety of devices that provide different functionalities. The second principal aspect is a method, typically in the form of software, operated using a data processing system (computer). The third principal aspect is a computer program product. The computer program product generally represents computer-readable instructions stored on a non-transitory computer-readable medium such as an optical storage device, e.g., a compact disc (CD) or digital versatile disc (DVD), or a magnetic storage device such as a floppy disk or magnetic tape. Other, non-limiting examples of computer-readable media include hard disks, read-only memory (ROM), and flash-type memories. These aspects will be described in more detail below.

A block diagram depicting an example of a system (i.e., computer system 100) of the present invention is provided in FIG. 1. The computer system 100 is configured to perform calculations, processes, operations, and/or functions associated with a program or algorithm. In one aspect, certain processes and steps discussed herein are realized as a series of instructions (e.g., software program) that reside within computer readable memory units and are executed by one or more processors of the computer system 100. When executed, the instructions cause the computer system 100 to perform specific actions and exhibit specific behavior, such as described herein.

The computer system 100 may include an address/data bus 102 that is configured to communicate information. Additionally, one or more data processing units, such as a processor 104 (or processors), are coupled with the address/data bus 102. The processor 104 is configured to process information and instructions. In an aspect, the processor 104 is a microprocessor. Alternatively, the processor 104 may be a different type of processor such as a parallel processor, application-specific integrated circuit (ASIC), programmable logic array (PLA), complex programmable logic device (CPLD), or a field programmable gate array (FPGA).

The computer system 100 is configured to utilize one or more data storage units. The computer system 100 may include a volatile memory unit 106 (e.g., random access memory ("RAM"), static RAM, dynamic RAM, etc.) coupled with the address/data bus 102, wherein a volatile memory unit 106 is configured to store information and instructions for the processor 104. The computer system 100 further may include a non-volatile memory unit 108 (e.g., read-only memory ("ROM"), programmable ROM ("PROM"), erasable programmable ROM ("EPROM"), electrically erasable programmable ROM "EEPROM"), flash memory, etc.) coupled with the address/data bus 102, wherein the non-volatile memory unit 108 is configured to store static information and instructions for the processor 104. Alternatively, the computer system 100 may execute instructions retrieved from an online data storage unit such as in "Cloud" computing. In an aspect, the computer system 100 also may include one or more interfaces, such as an interface 110, coupled with the address/data bus 102. The one or more interfaces are configured to enable the computer system 100 to interface with other electronic devices and computer systems. The communication interfaces implemented by the one or more interfaces may include wireline (e.g., serial cables, modems, network adaptors, etc.) and/or wireless (e.g., wireless modems, wireless network adaptors, etc.) communication technology.

In one aspect, the computer system 100 may include an input device 112 coupled with the address/data bus 102, wherein the input device 112 is configured to communicate information and command selections to the processor 100. In accordance with one aspect, the input device 112 is an alphanumeric input device, such as a keyboard, that may include alphanumeric and/or function keys. Alternatively, the input device 112 may be an input device other than an alphanumeric input device. In an aspect, the computer system 100 may include a cursor control device 114 coupled with the address/data bus 102, wherein the cursor control device 114 is configured to communicate user input information and/or command selections to the processor 100. In an aspect, the cursor control device 114 is implemented using a device such as a mouse, a track-ball, a track-pad, an optical tracking device, or a touch screen. The foregoing notwithstanding, in an aspect, the cursor control device 114 is directed and/or activated via input from the input device 112, such as in response to the use of special keys and key sequence commands associated with the input device 112. In an alternative aspect, the cursor control device 114 is configured to be directed or guided by voice commands.

In an aspect, the computer system 100 further may include one or more optional computer usable data storage devices, such as a storage device 116, coupled with the address/data bus 102. The storage device 116 is configured to store information and/or computer executable instructions. In one aspect, the storage device 116 is a storage device such as a magnetic or optical disk drive (e.g., hard disk drive ("HDD"), floppy diskette, compact disk read only memory ("CD-ROM"), digital versatile disk ("DVD")). Pursuant to one aspect, a display device 118 is coupled with the address/data bus 102, wherein the display device 118 is configured to display video and/or graphics. In an aspect, the display device 118 may include a cathode ray tube ("CRT"), liquid crystal display ("LCD"), field emission display ("FED"), plasma display, or any other display device suitable for displaying video and/or graphic images and alphanumeric characters recognizable to a user.

The computer system 100 presented herein is an example computing environment in accordance with an aspect. However, the non-limiting example of the computer system 100 is not strictly limited to being a computer system. For example, an aspect provides that the computer system 100 represents a type of data processing analysis that may be used in accordance with various aspects described herein. Moreover, other computing systems may also be implemented. Indeed, the spirit and scope of the present technology is not limited to any single data processing environment. Thus, in an aspect, one or more operations of various aspects of the present technology are controlled or implemented using computer-executable instructions, such as program modules, being executed by a computer. In one implementation, such program modules include routines, programs, objects, components and/or data structures that are configured to perform particular tasks or implement particular abstract data types. In addition, an aspect provides that one or more aspects of the present technology are implemented by utilizing one or more distributed computing environments, such as where tasks are performed by remote processing devices that are linked through a communications network, or such as where various program modules are located in both local and remote computer-storage media including memory-storage devices.

Figure 2:
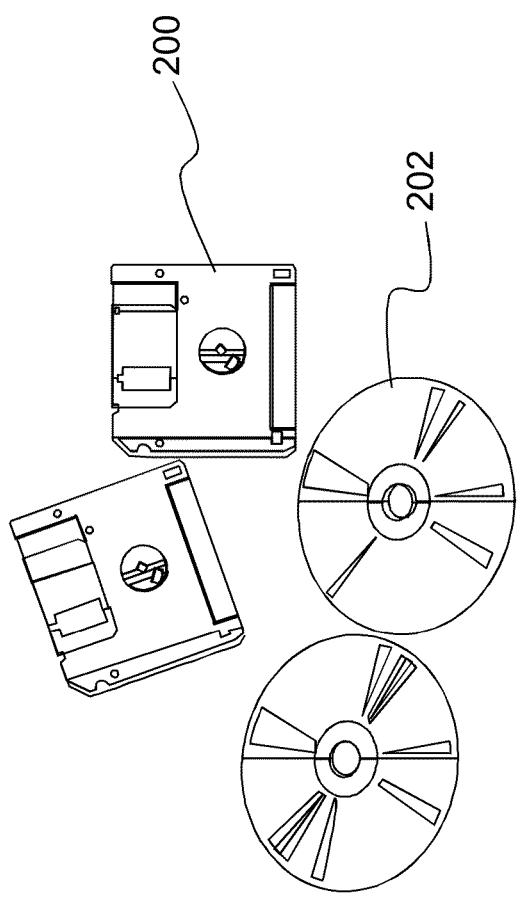
FIG. 2 is an illustration of a computer program product according to some embodiments of the present disclosure.

An illustrative diagram of a computer program product (i.e., storage device) embodying the present invention is depicted in FIG. 2. The computer program product is depicted as floppy disk 200 or an optical disk 202 such as a CD or DVD. However, as mentioned previously, the computer program product generally represents computer-readable instructions stored on any compatible non-transitory computer-readable medium. The term "instructions" as used with respect to this invention generally indicates a set of operations to be performed on a computer, and may represent pieces of a whole program or individual, separable, software modules. Non-limiting examples of "instruction" include computer program code (source or object code) and "hard-coded" electronics (i.e. computer operations coded into a computer chip). The "instruction" is stored on any non-transitory computer-readable medium, such as in the memory of a computer or on a floppy disk, a CD-ROM, and a flash drive. In either event, the instructions are encoded on a non-transitory computer-readable medium.

Specific Details of Various Embodiments

Figure 3A:
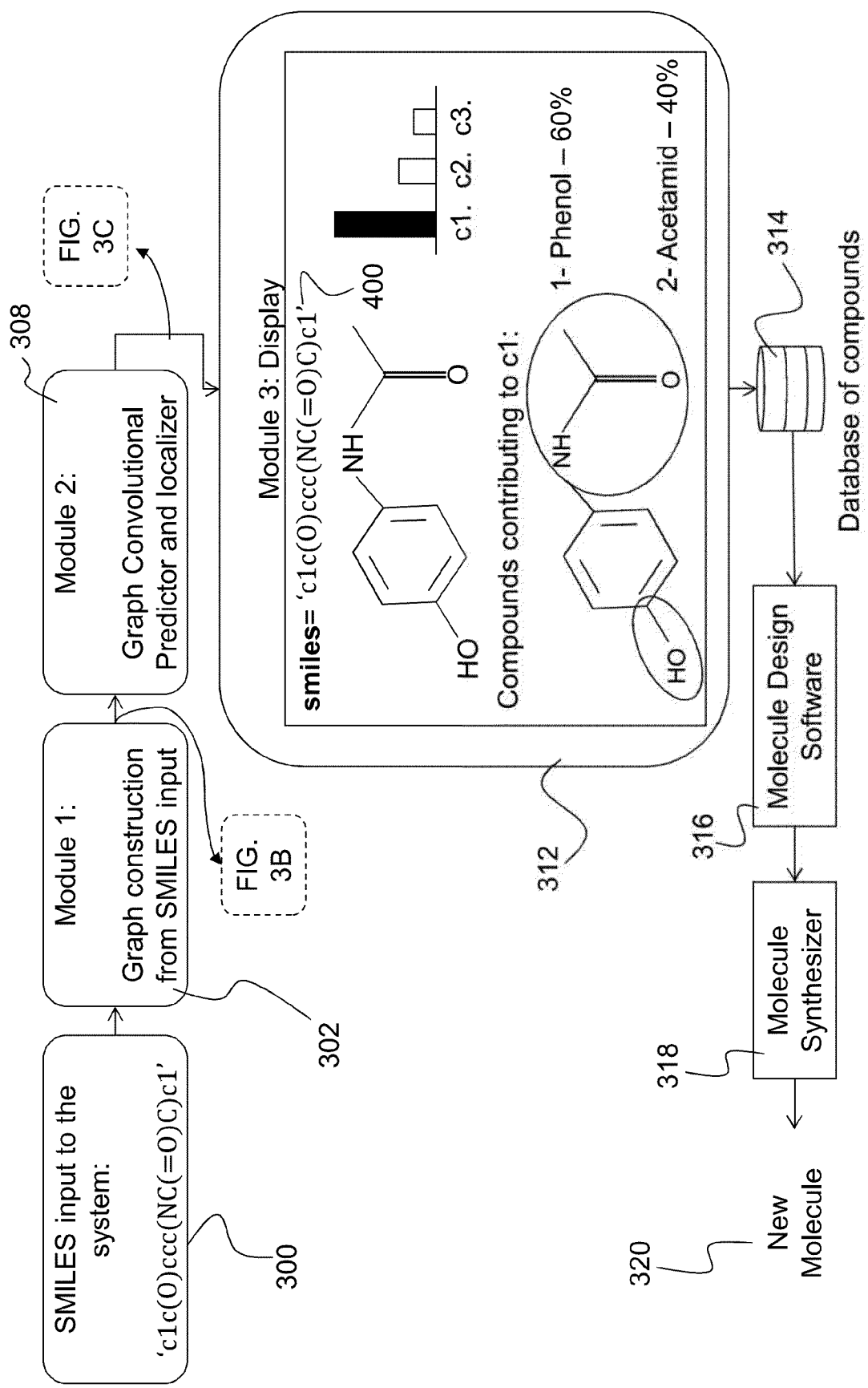
FIG. 3A is an illustration of the system architecture for a system for automatically identifying chemical properties of a molecule according to some embodiments of the present disclosure.
Figure 3B:
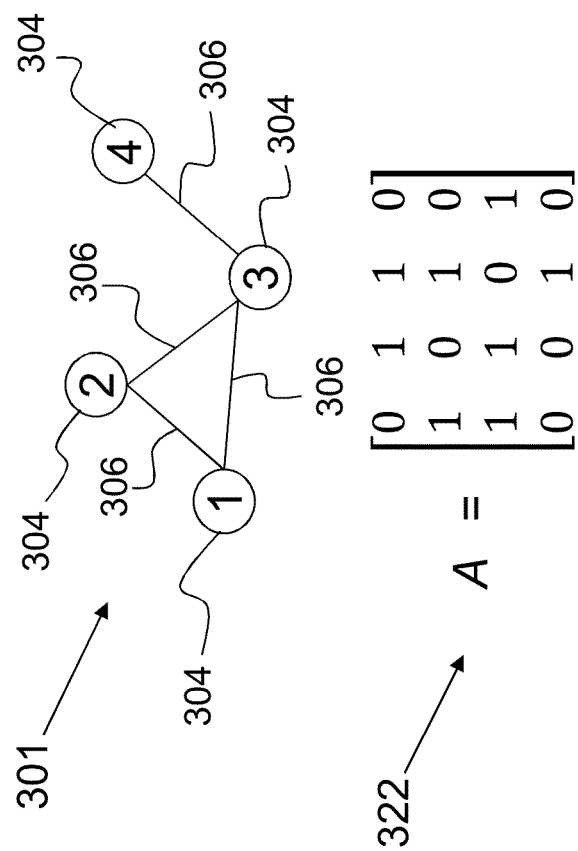
FIG. 3B is an illustration of the graph translated from a a Simplified Molecular-Input Line-Entry System (SMILES) representation according to some embodiments of the present disclosure.
Figure 3C:
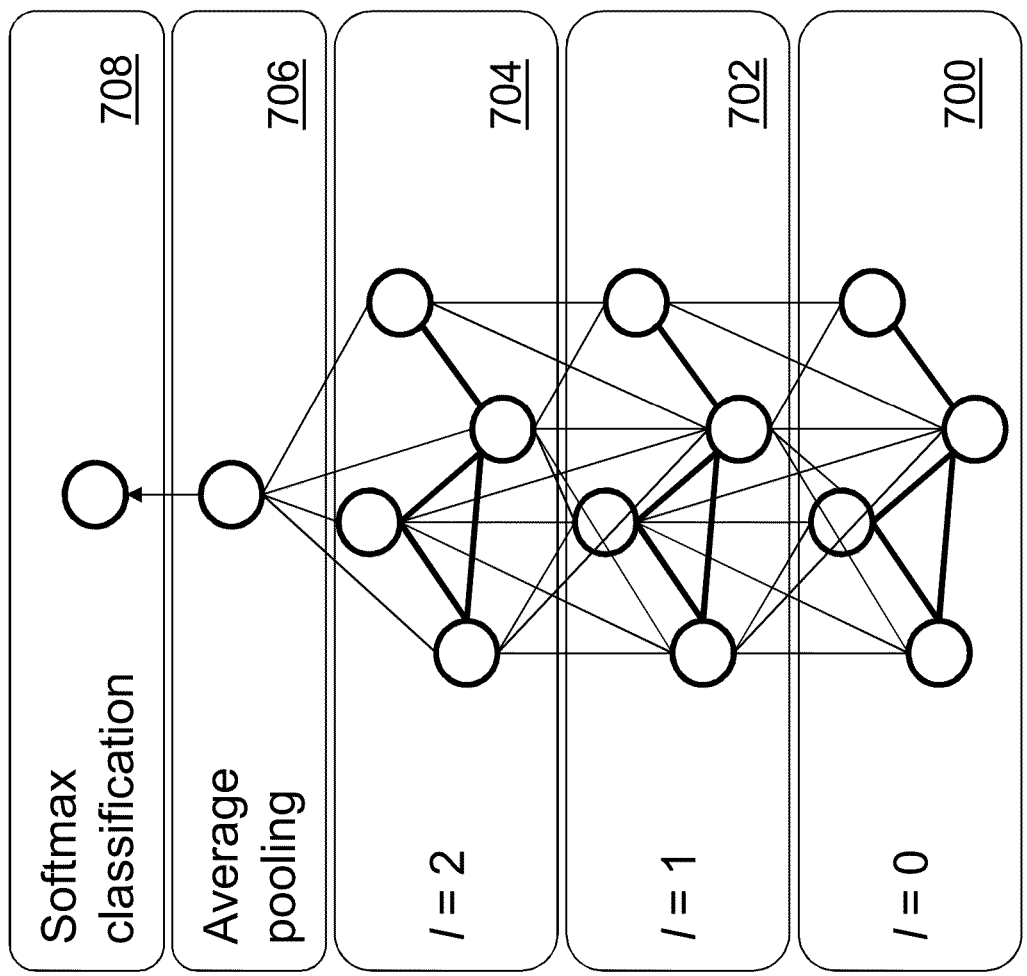
FIG. 3C is an illustration of a specialized graph convolutional neural network according to some embodiments of the present disclosure.

Described is a method for identifying the chemical properties of a molecule and localizing the molecular compounds (sub-structures) that contribute to the identified properties. FIGS. 3A-3C show the overall architecture of the system described herein. The system receives as input (element 300) the Simplified Molecular-Input Line-Entry System (SMILES) (see Literature Reference No. 1) representation of a molecule and identifies 1) whether it contains certain chemical characteristics or not (e.g., toxicity), and 2) localizes the parts of the molecule (i.e., atoms and compounds) that contribute to the identified characteristic. The SMILES representation of a molecule is a commonly used specification in form of a line notation for describing the structure of chemical species using short ASCII strings.

Figure 4:
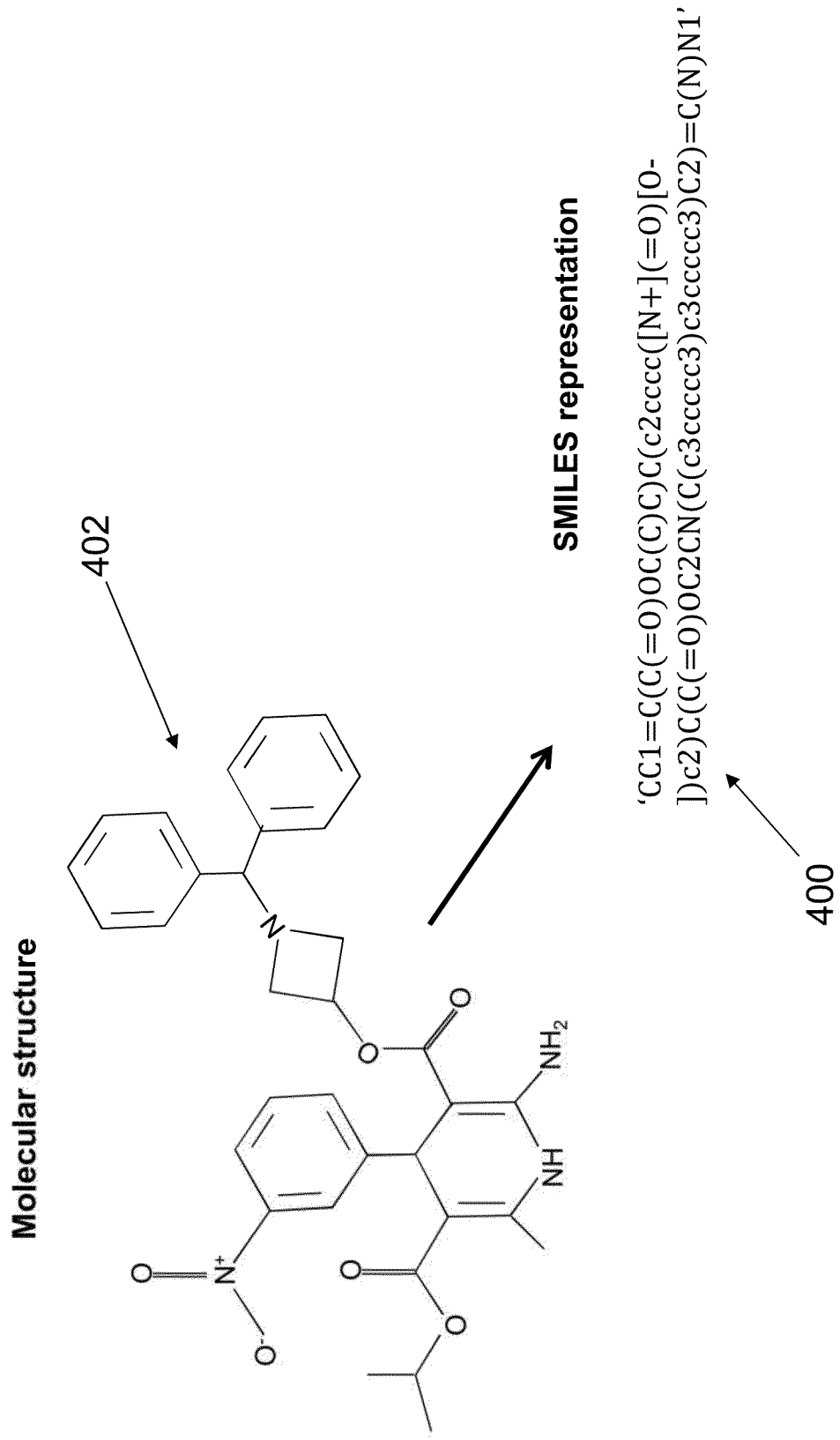
FIG. 4 is an illustration of a SMILES representation of a random organic molecule according to some embodiments of the present disclosure.

Three modules provide a three-step process. The first module (element 302) translates the SMILES representation of the molecule into a graph (element 301 in FIG. 3B), where the nodes (element 304) of the graph (element 301) represent different atoms, and the edges (element 306) represent the chemical bonds. The second module (element 308) comprises a specialized graph convolutional neural network (element 310 in FIG. 3C) that predicts the chemical characteristic of the input molecule and identifies the atoms/compounds that contribute to that chemical characteristic. The third module (element 312) contains a display that lists and visualizes the compounds in the molecule that cause the molecule to have certain chemical characteristics. Then, the third module (element 312) stores these compounds in a database (element 314). As a result, the database (element 314) can be used by molecule design software (element 316) to design molecules with certain desired properties. Given a design, these molecules can be built with a molecule synthesizer (element 318) to synthesize a new molecule (element 320). Literature Reference No. 7 provides a description of an example of a molecule synthesizer. FIG. 4 illustrates an example SMILES representation (element 400) of a molecular structure (element 402).

The invention described herein facilitates the design and synthesis of molecules that satisfy certain chemical characteristics, and decreases or avoids expensive experimental tests in the design process. Today, many applications seek novel molecular structures (e.g., micro-electronics, vehicle and aircraft coatings, chemical warfare, pharmaceutical applications), which satisfy certain chemical characteristics. The search for these novel molecular structures relies heavily on trial and error, which comes at a huge cost due to often expensive experimental setups.

The system according to embodiments of the present disclosure is a unique machine learning system that learns to predict chemical characteristics of different molecules and, moreover, localizes the compounds that contribute to the identified characteristics. Therefore, the system described herein provides a framework for not only predicting the potential characteristics of a molecular structure, but also guiding the scientists in the design process by providing them with the list of compounds that are causing or preventing the presence of certain chemical characteristics.

(3.1) Module 1: Graph Construction From SMILES Input (Element 302)

The SMILES string (element 400) is the input (element 300) to the first module (element 302), which transforms the SMILES representation (element 400) in the form of a graph (element 301; FIG. 3B). In the SMILES representation (element 400), atoms are represented by their atomic symbols, while hydrogen atoms are omitted (as they are implicitly represented via SMILES notation). Neighboring atoms are represented next to each other and branches are represented by parentheses. Finally, to avoid redundant representations, the SMILES representation (element 400) orders the atoms by the number of bonds they share with other atoms.

Figure 5:
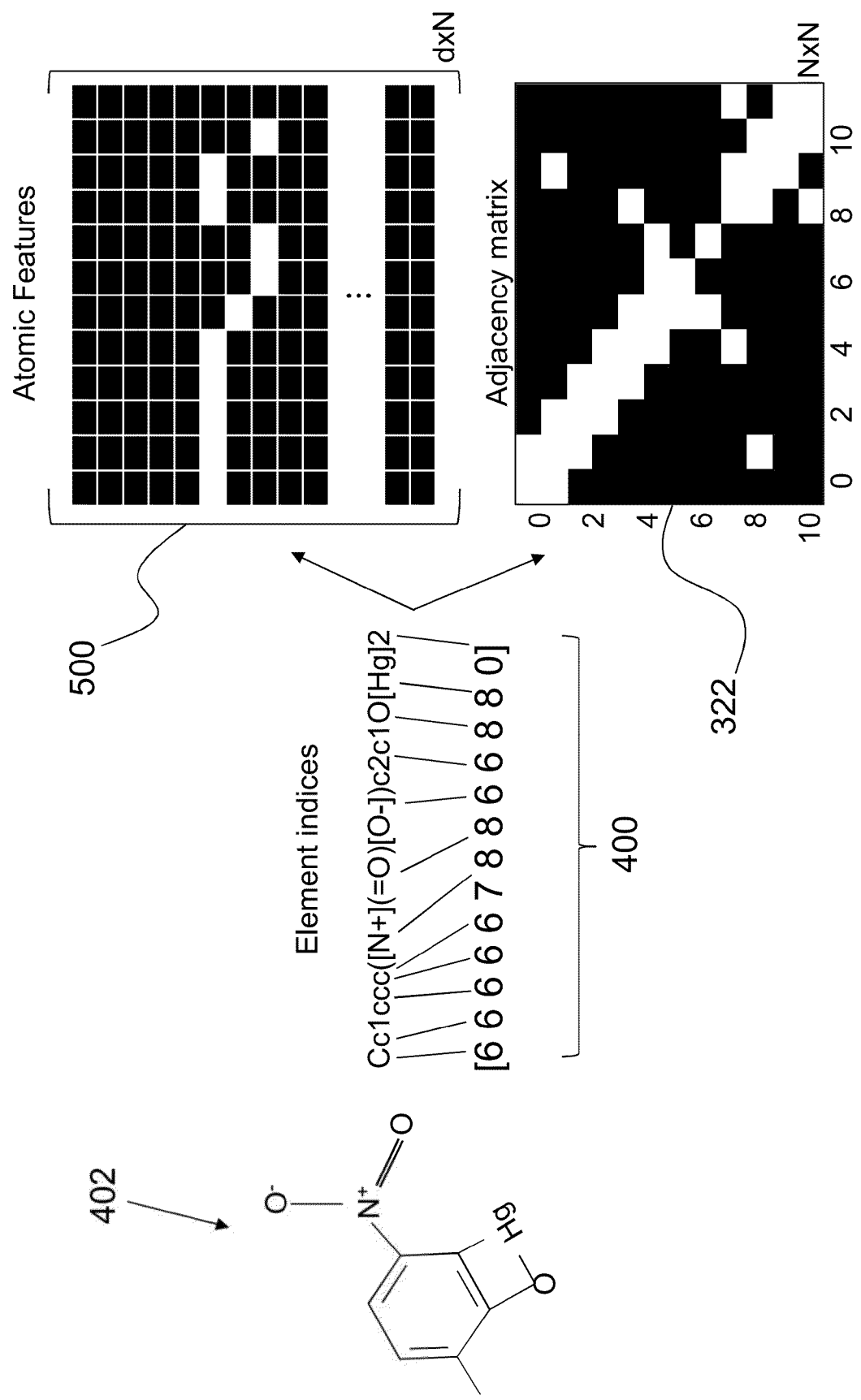
FIG. 5 is an illustration of conversion of a SMILES representation into atomic features and adjacency matrices according to some embodiments of the present disclosure.

A molecular structure is equivalent to a mathematical graph, where each atom is a node (element 304), and each bond is an edge (element 306). Such representation allows for applying graph theory and mathematical processes to molecular structures (e.g., element 402). To create a graph, the SMILES representation (element 400) is first parsed (following the standard protocol for SMILES representation, which is described in Literature Reference Nos. 1 and 6) to obtain atomic numbers of the atoms in the molecule. Next, a d-dimensional atomic feature is constructed for each atom leading to a N × d matrix, where N is the number of atoms in a molecule. Consider 109 stable atoms, the atomic feature x, could, for instance, be a one-hot vector indicating the atomic number for one of these 109 atoms. For instance, for a carbon atom C, x could be a 109-dimensional vector with all zeros, except a "1" at the atomic number of C (i.e., 6). In this example, the magnitude of d is always 1. The described atomic feature only captures the atom type. More sophisticated atomic features could be utilized here that describe other characteristics of the atom, such as number of ionic or covalent bonds. Finally, following the SMILES representation, an adjacency matrix (element 322; FIG. 3B) is constructed to reflect the bonds between the atoms. The adjacency matrix (element 322) is an N × N binary matrix, where the [i,j]th element of the matrix indicates whether atom i has a bond with atom j. FIG. 5 illustrates how Module 1 receives a SMILES representation (element 400) and converts it into atomic features (element 500) and an adjacency matrix (element 322).

(3.2) Module 2: Graph Convolutional Predictor and Localizer (Element 308)

Figure 6:
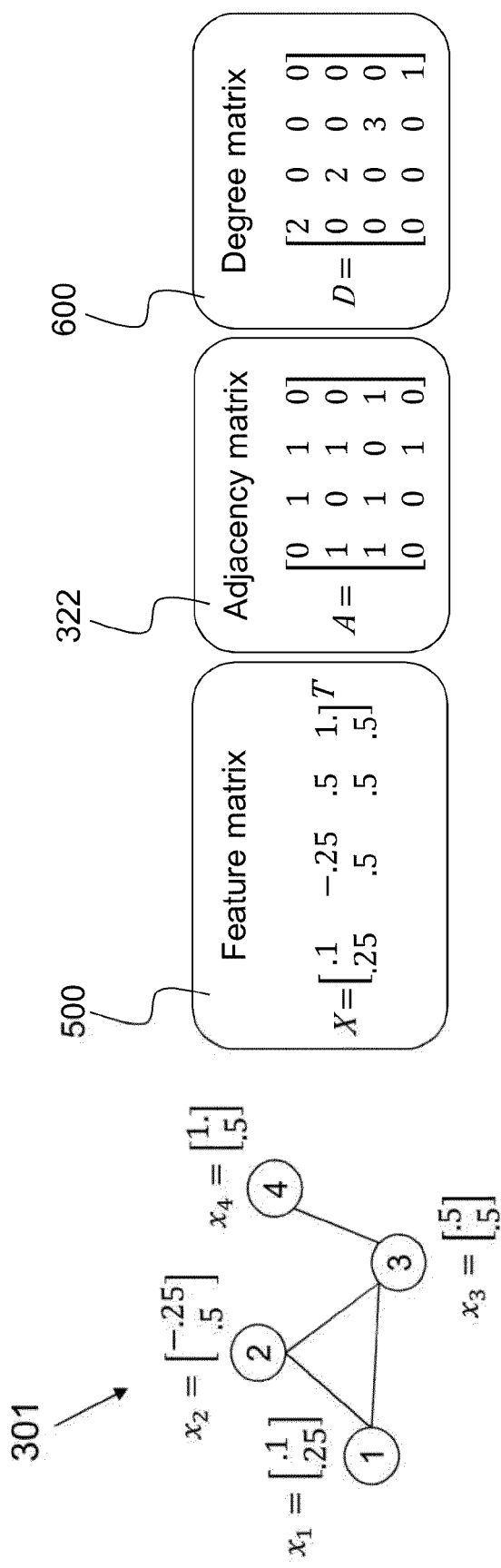
FIG. 6 is an illustration of a feature matrix, an adjacency matrix, and a degree matrix for a simple input graph according to some embodiments of the present disclosure.

The inputs to module 2 (element 308) are the atomic features and the corresponding adjacency matrix (element 322) for the input molecule (e.g., element 402). Let $x_i \in \mathbb{R}^d$ be the input features for the i'th node in the graph and let $X = [x_i]_{i=0}^N$ represent the matrix of atomic features (element 500) obtained from Module 1 (element 302). In addition, let A denote the adjacency matrix (element 322), which is a binary matrix with elements $A_{i,j}$ indicating whether node i and node j are connected. Following classic graph theory, the degree matrix D (element 600 in FIG. 6) is defined as a diagonal matrix where $D_{i,i} = \Sigma_j A_{i,j}$. FIG. 6 depicts an intuitive visualization of a simple graph (element 301) with d = 2 and N = 4 and its corresponding atomic feature matrix (element 500), adjacency matrix (element 322), and degree matrix (element 600).

Figure 7:
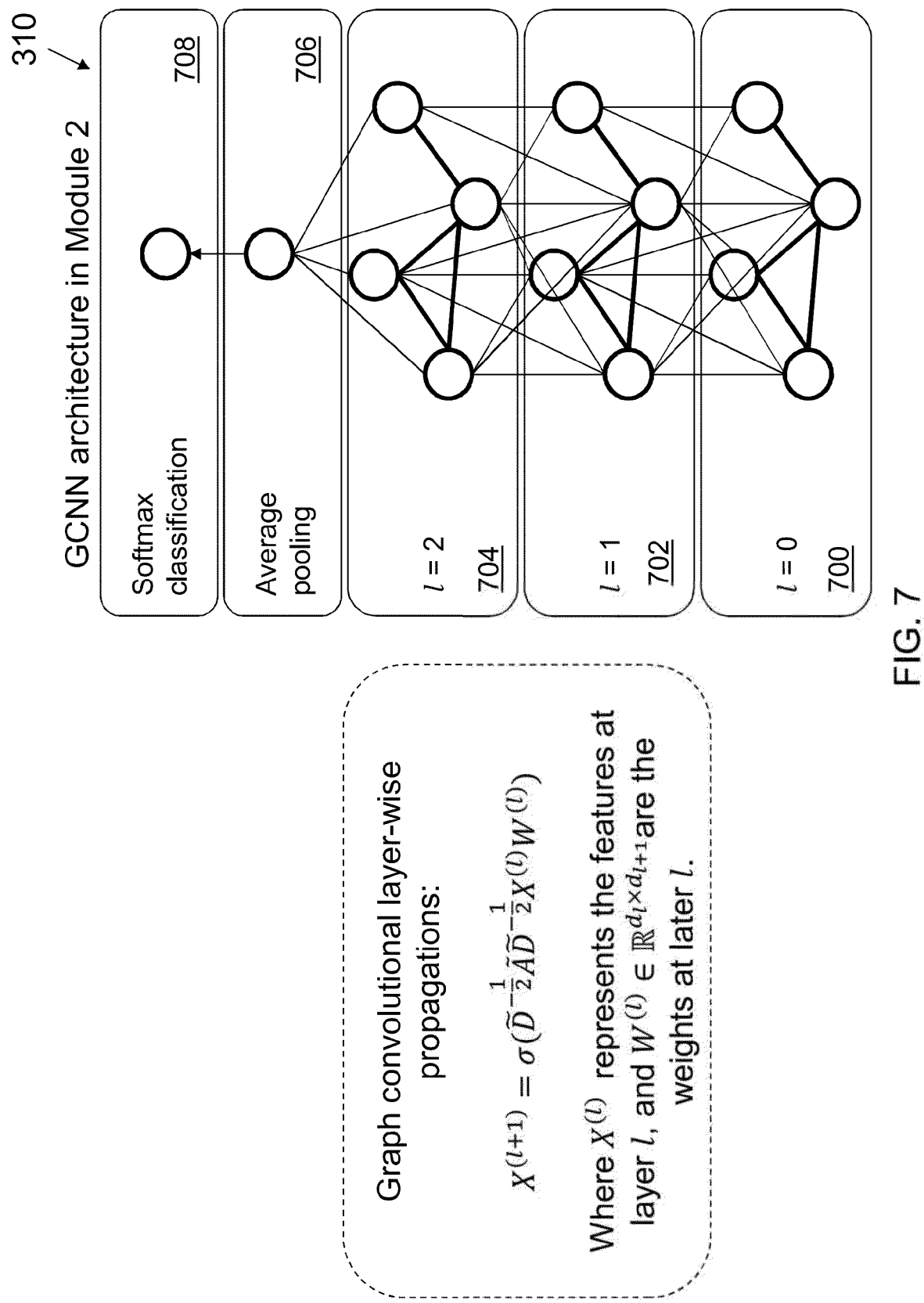
FIG. 7 is an illustration of the architecture of a graph-convolutional neural network (GCNN) according to some embodiments of the present disclosure.

Following the work of Kipf et al. (see Literature Reference No. 2), a graph-convolutional neural network (GCNN) (element 310) is utilized on top of the molecule graph. Let $X^{(l)}$ denote the feature matrix of the graph at the l'th layer of the GCNN (element 310), where $X^{(0)} = X$ is the feature matrix of the graph extracted in Module 1 (element 302). The GCNN (element 310) then propagates the features at each layer using:

$$X^{(l+1)} = \sigma\left(\tilde{D}^{-\frac{1}{2}} \tilde{A} \tilde{D}^{-\frac{1}{2}} X^{(l)} W^{(l)}\right), \quad (1)$$

where $$\tilde{A} = A + I, \tilde{D}_{ii} = \Sigma_j \tilde{A}_{ij}, W^{(l)}$$

are the neural kernels/weights that will be trained during the training phase, I represents an identity matrix of the same size as A, and $\sigma(\cdot)$ is a nonlinear activation function used in the GCNN (element 310) (e.g., sigmoid function $\sigma(t) = \frac{1}{1+e^{-t}}$). Equation (1) provides the basis for the second module (element 308). The specific architecture for the GCNN (element 310) is depicted in FIG. 7.

Briefly, L (e.g., L = 3) convolutional layers (elements 700, 702, and 704) are followed by an average pooling layer (element 706) and a Softmax classifier layer (element 708). Let $X^{(L)}$ be the feature matrix (element 500) of size $N \times d_L$ at the final convolutional layer (e.g., l=2 (element 704)). The dimensionality of the atomic feature changes from one convolutional layer to another. Note that different molecules will have different number of atoms, N, and therefore they lead to matrices $X^{(L)}$ of different sizes (i.e., different number of rows). To deal with the dynamic nature of molecule size, a global average pooling (element 706) is utilized as $\bar{x}_j = \frac{1}{N}\sum_{n=1}^N X_{n,j}^{(L)}$. Therefore, $\bar{x}$ becomes a $d_L$ dimensional vector regardless of the input graph size. Finally, the Softmax classifier (element 708) or linear regression is performed on $\bar{x}$ for classification and/or regression tasks. This step is equivalent to $$y = \sum_{j=1}^{d_L} \omega_j \bar{x}_j + \omega_0, \quad (2)$$

where y is the objective chemical characteristic (e.g., toxicity level), and $\omega_j$s are softmax classifier parameters to be learned (as discussed below). Moreover, rewriting Equation (2) in terms of $X^{(L)}$, the following is obtained:

$$y = \frac{1}{N}\sum_{n=1}^N \underbrace{\left(\sum_{j=1}^{d_L} \omega_j X_{n,j}^{(L)} + \omega_0\right)}_{\hat{x}_n}. \quad (3)$$

From Equation (3) it can be seen that the prediction y is essentially an average over parameter $\hat{x}_n = \sum_{j=1}^{d_L} \omega_j X_{n,j}^{(L)} + \omega_0$. As can be seen, the value of $\hat{x}_n$ indicates the importance of the n'th atom in the molecule for predicting the chemical characteristic y. Hence, $\hat{x}$ assigns a score to each atom of a molecule, and localizes the important parts/compounds/atoms of the molecules that correspond to certain chemical characteristic.

(3.3) Module 3: Molecule Display and Design (Element 312)

Module 3 (element 312) receives the SMILES representation (element 400) as well as the predicted characteristic y, and $\hat{x}$ from Module 2 (element 308). This module (element 312) visualizes the molecule, reports the predicted chemical characteristic, and visualizes a heat-map on the molecular structure that identifies the importance of groups of atoms for the predicted characteristic. As known by one skilled in the art, a heat-map is a representation of data in the form of a map or diagram in which data values are represented as colors. Linked groups of atoms with high importance for a given characteristic form a key compound that is stored in a database (element 314) together with its characteristic.

A human, for example, could identify such compounds on the display based on the heat-map. This database (element 314) may be augmented with known molecule compounds and their characteristics. A molecule design software (element 316) may retrieve compounds from the database (element 314) and optimize the design based on given specifications (e.g., list of chemical properties). Non-limiting examples of molecule design software include Maestro produced by Schrödinger (located at 120 West 45th Street, 17th Floor, New York, NY 10036) and software produced by Chemical Computing Group (located at 910-1010 Sherbrooke St. W., Montreal, QC H3A 2R7, Canada).

Given a design, a machine (i.e., a molecule synthesizer (element 318)) automatically synthesizes the molecules (element 320). For instance, an automated machine can synthesize a range of small organic molecules with the push of a button. The synthesizer uses a chemical method that pieces together molecules from modular building blocks that can be put together in any configuration. The molecule synthesizer can include a suite of modules in a laboratory, where each module performs a different operation, such as cooling, heating, sample preparation, and analytics. A non-limiting example of a machine to synthesize molecules is described in Li et al., 2015 (see Literature Reference No. 3).

(3.4) Training Phase

The second module (element 308) contains a GCNN (element 310) that requires training to obtain optimal parameters, $W^{(l)}$, for l = 1, ..., L and $\omega_j$, for j = 0, ..., $d_L$, where L represents a total number of convolutional layers, and $\omega_j$ represents a softmax classifier parameter (see element 708 in FIG. 3C) after the average pooling (i.e., the parameters from average pooling (element 706) to softmax classification (element 708).

To train these parameters, a mean squared error loss function is minimized as follows:

$$argmin_{W^{(l)},\omega} \sum_k \left\| \frac{1}{N} \sum_{n=1}^{N} \underbrace{\left( \sum_{j=1}^{d_L} \omega_j \left( X^k \right)_{n,j}^{(L)} + \omega_0 \right)}_{\hat{x}_n} - y^k \right\|_2^2,$$

where $(X^k)^{(0)}$ is the atom features from the k'th molecule in the training set, $y^k$ is the ground truth chemical characteristic, and $(X^k)^{(l+1)} = \sigma\left( \left( \widetilde{D}^k \right)^{-\frac{1}{2}} \left( \widetilde{A}^k \right) \left( \widetilde{D}^k \right)^{-\frac{1}{2}} \left( X^k \right)^{(l)} W^{(l)} \right)$ Optimal parameters are then found using back-propagation (i.e., gradient descent).

(3.5) Experimental Studies

Figure 8A:
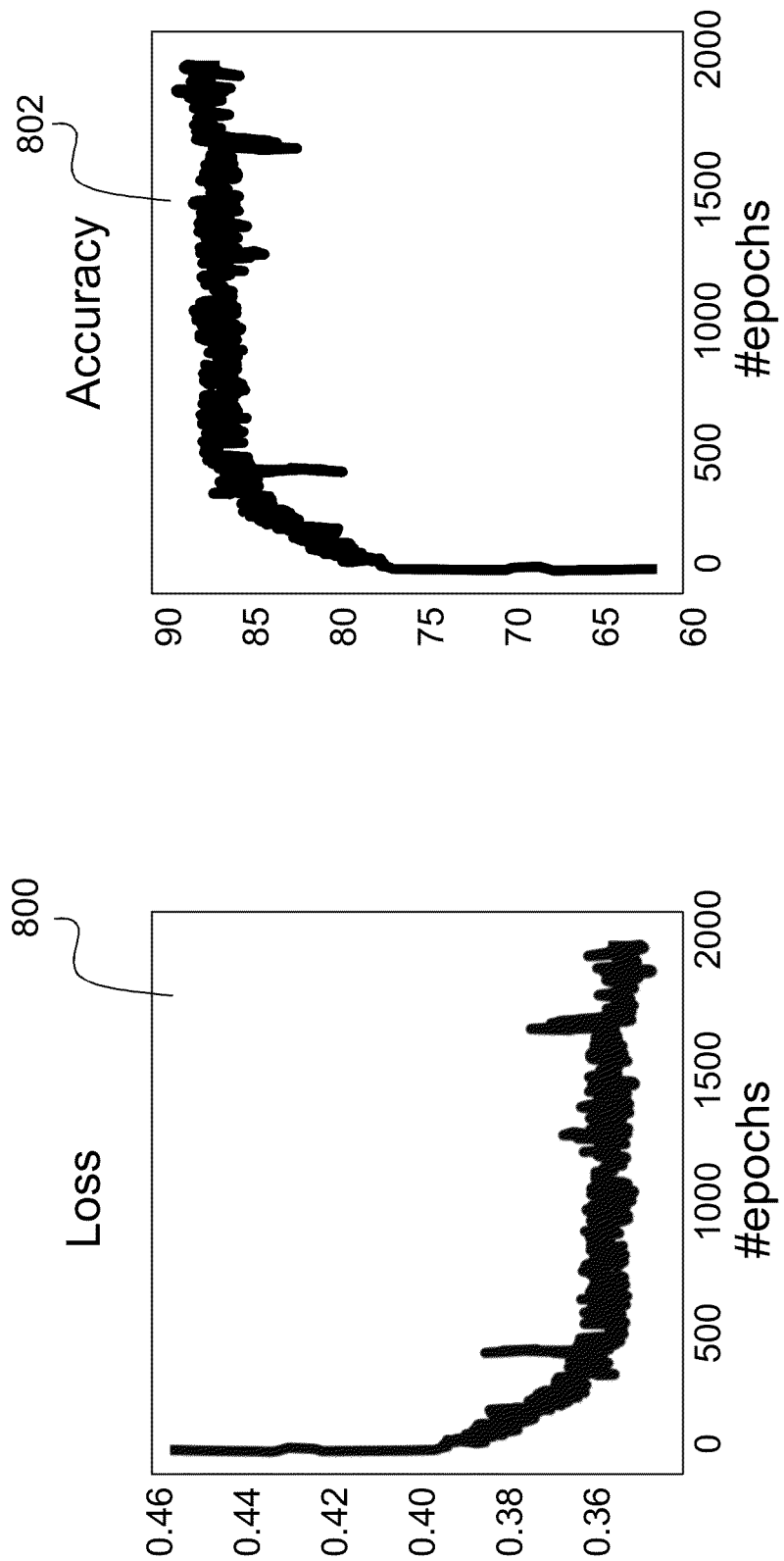
FIG. 8A is an illustration of loss and test accuracy results for the system according to some embodiments of the present disclosure.
Figure 8B:
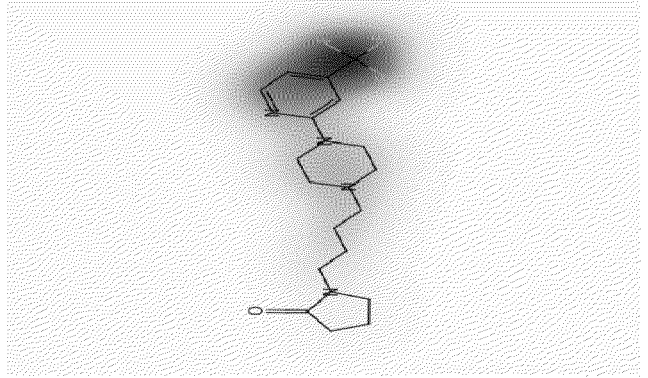
FIG. 8B is an illustration of sample localization results for Trifluoromethyl according to some embodiments of the present disclosure.
Figure 8B:
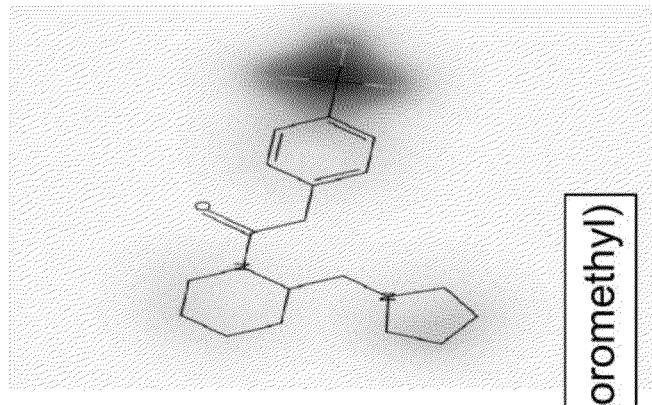
Figure 8B:
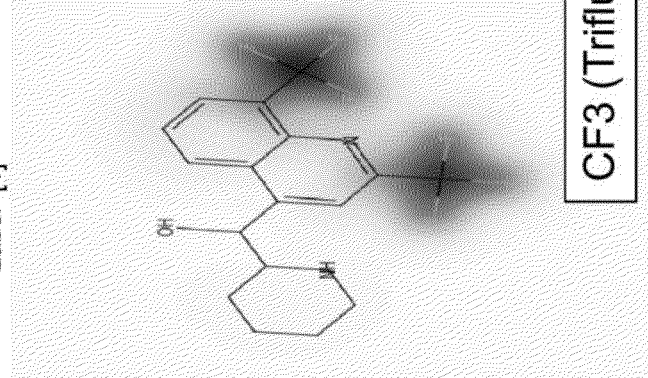
Figure 8B:
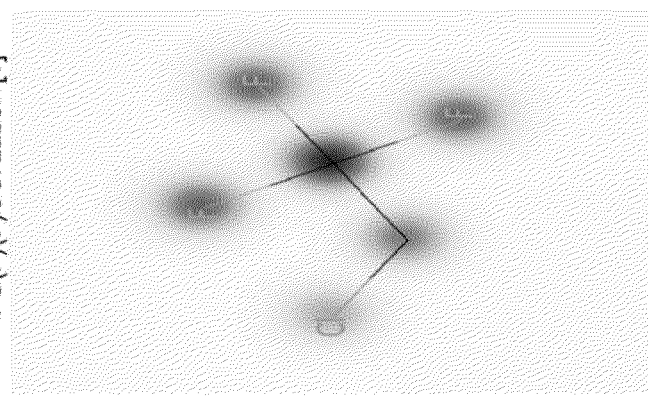
Figure 8C:
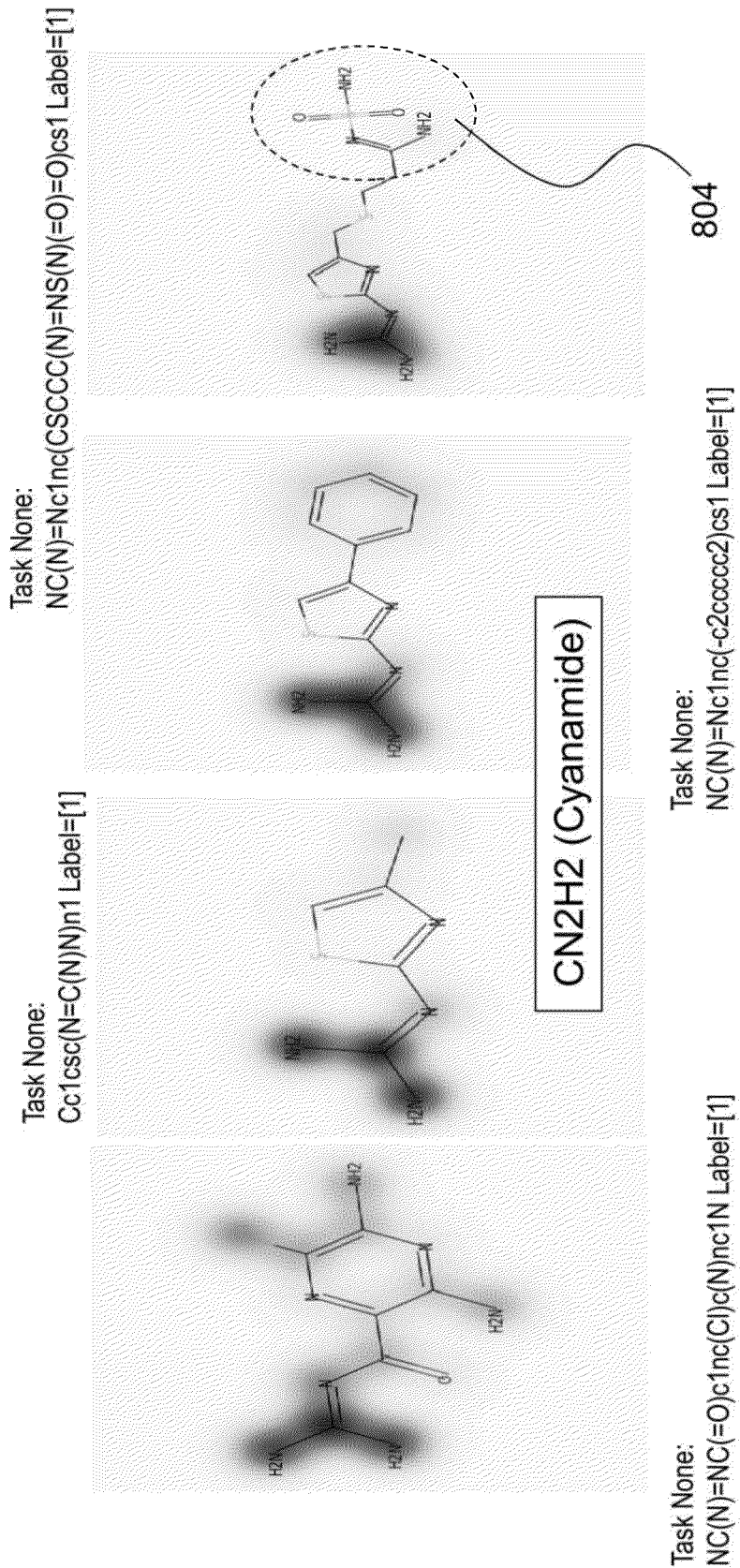
FIG. 8C is an illustration of sample localization results for Cyanamide according to some embodiments of the present disclosure.

The invention according to embodiments of the present disclosure was applied to the Blood-Brain Barrier Penetration (BBBP) molecule dataset (see Literature Reference No. 6), which contains 2039 pharmaceutical molecules with labels indicating whether the molecule is capable of penetrating the blood-brain barrier or not. The system described herein was trained on 80% of the dataset, and the classification accuracy was reported on the remaining 20% test set. Moreover, the method described herein was tested for localization of the chemical compounds contributing to BBBP. FIG. 8A shows plots of training loss (element 800) and testing accuracy (88.87%) (element 802). An epoch is a training cycle in which the neural network is exposed to all instances in the training set. FIG. 8B is an illustration of sample localization results for trifluoromethyl, and FIG. 8C is an illustration of sample localization results for cyanamide.

The machine learning system described herein has learned to identify the important substructure in a molecule for a particular function, such as "being toxic", or "being able to pass the blood-brain-barrier". The system can sift through millions of molecules in a short amount of time (e.g., order of several hours) and find the common molecular substructures that correspond to a certain function, which would be infeasible for a human to do. Furthermore, the system according to embodiments of the present disclosure can also help with scientific discovery of functional groups (i.e., molecular substructures corresponding to a certain function). For instance, CF3 and CN2H2 in FIGS. 8B and 8C, respectively, are found among thousands of possible atomic substructures existing in the dataset. The Sulphonamide group (SO2NH2) (element 804) in the molecule in FIG. 8C is also a molecular substructure that repeats many times in the dataset, however, it doesn't contribute to the functional class of interest, hence, the system and method described herein does not highlight it. The knowledge that CN2H2 contributes to the functional class but SO2NH2 does not is purely mined by the machine learning system according to embodiments of the present disclosure.

Designing new molecular structures that fulfill desired objectives is a key requirement in various research arenas including material sciences, chemical engineering, and pharmaceutical research. A system that can guide scientists in the design process is of high value in the aforementioned fields. In addition, such systems are of high interest for any research and development (R&D) lab working on material sciences (e.g., for engineering novel adhesives or surface coatings), and military labs (e.g., for creating chemical-specific sensors).

Automatic localization of chemical compounds in a molecule has not been done before. In addition, simultaneous prediction of chemical characteristics and compounds localization has not been done before. Prior works on predictive modeling that use the physicochemical properties and structural motifs of a chemical to reduce hazards (e.g., toxicity) through molecular design have relied on detailed knowledge and models about the human body's absorption, distribution, metabolism, and excretion of chemicals (see Literature Reference No. 4). In contrast, the invention described herein does not require a priori knowledge about human physiology, and instead automatically learns to predict the physiochemical properties and relevant structural motifs.

Another branch of work focuses on using machine learning to accelerate human designed and executed experiments for materials design. For example, in Literature Reference No. 5, a new method is proposed to automatically identify distinct x-ray diffraction patterns that are indicative of unique materials, which is normally done by hand. In contrast, the system according to embodiments of the present disclosure is focused on automatically identifying molecular subsubstructures that have distinct chemical effects. Additionally, the invention described herein can be used to identify molecular compounds that, when combined, lead to specific material-level properties (e.g., stiffness, hardness, conductivity).

Finally, while this invention has been described in terms of several embodiments, one of ordinary skill in the art will readily recognize that the invention may have other applications in other environments. It should be noted that many embodiments and implementations are possible. Further, the following claims are in no way intended to limit the scope of the present invention to the specific embodiments described above. In addition, any recitation of "means for" is intended to evoke a means-plus-function reading of an element and a claim, whereas, any elements that do not specifically use the recitation "means for", are not intended to be read as means-plus-function elements, even if the claim otherwise includes the word "means". Further, while particular method steps have been recited in a particular order, the method steps may occur in any desired order and fall within the scope of the present invention.

What is claimed is:

1. A system for automatically identifying chemical properties of a molecule, the system comprising:
one or more processors and a non-transitory computer-readable medium having executable instructions encoded thereon such that when executed, the one or more processors perform an operation of:
converting a chemical representation of a molecular structure into a graph, wherein each node of the graph represents an atom in the chemical representation, and each edge of the graph represents a chemical bond in the chemical representation;
generating a d-dimensional atomic feature for each atom, resulting in a N x d matrix, where N a number of atoms in the molecular structure;
generating a binary adjacency matrix A for each chemical bond with elements $A_{i,j}$ indicating whether a node i and a node j are connected via a chemcial bond;

propagating the atomic features at each layer of a graph-convolutional neural network (GCNN) according to the following:

$$X^{(l+1)} = \sigma\left(\tilde{D}^{-\frac{1}{2}} \tilde{A} \tilde{D}^{-\frac{1}{2}} X^{(l)} W^{(l)}\right),$$

where $$\tilde{A} = A + I, \ \tilde{D}_{ii} = \Sigma_j \tilde{A}_{ij} \text{ and } \tilde{D}_{ij} = 0$$

for $i \neq j$, I represents an identity matrix of the same size as A, l represents a convolutional layer in the GCNN, $X^{(l)}$ represents the atomic features at layer l, $W^{(l)}$ represents neural weights, and $\sigma(\cdot)$ is a nonlinear function used in the GCNN;

assigning a score $\hat{x}_n$ to each atom indicating its importance for predicting a given chemical characteristic y, wherein $\hat{x}_n$ is determined according to the following:

$$\hat{x}_n = \sum_{j=1}^{d_L} \omega_j X_{n,j}^{(L)} + \omega_0,$$

where $X^{(L)}$ is a feature matrix of size $N \times d_L$ and $w_j$ and $w_o$ are softmax classifier parameters;

generating a visual representation of the molecular structure based on the chemical representation, $\hat{x}_n$, and y;

identifying groups of atoms for the given chemical characteristic from the visual representation;

storing the identified groups of atoms for the given chemical characteristic in a database; and designing a new molecule having the given chemical characteristic based on the stored identified groups of atoms.

2. The system as set forth in claim 1, wherein the one or more processors further perform an operation of causing a molecule synthesizer to synthesize the new molecule.

3. The system as set forth in claim 1, wherein the one or more processors further perform an operation of predicting a chemical characteristic of an input molecular structure without a priori knowledge.

4. The system as set forth in claim 1, wherein the one or more processors further performs an operation of training the neural network to obtain parameters $W^{(l)}$, for l = 1, ..., L and $\omega_j$, for j = 0, ..., $d_L$, where L represents a total number of convolutional layers, where $\omega_j$ represents a softmax classifier parameter, and wherein a mean squared error loss function is minimized as follows:

$$argmin_{W^{(l)}, \omega} \sum_k \left\| \frac{1}{N} \sum_{n=1}^{N} \underbrace{\left(\sum_{j=1}^{d_L} \omega_j \left(X^k\right)_{n,j}^{(L)} + \omega_0\right)}_{\hat{x}_n} - y^k \right\|_2^2,$$

where $(X^k)^{(0)}$ represents atomic features from a k'th molecular structure in a training set, $d_L$ is a dimension of the atomic feature in the $L^{th}$ layer, $y^k$ is a ground-truth chemical characteristic, and $(X^k)^{(l+1)} = \sigma\left(\left(\tilde{D}^k\right)^{-\frac{1}{2}} \left(\tilde{A}^k\right) \left(\tilde{D}^k\right)^{-\frac{1}{2}} \left(X^k\right)^{(l)} W^{(l)}\right).$ 5. A computer implemented method for automatically identifying chemical properties of a molecule, the method comprising an act of:

causing one or more processors to execute instructions encoded on a non-transitory computer-readable medium, such that upon execution, the one or more processors perform operations of:

converting a chemical representation of a molecular structure into a graph, wherein each node of the graph represents an atom in the chemical representation, and each edge of the graph represents a chemical bond in the chemical representation;

generating a d-dimensional atomic feature for each atom, resulting in a N × d matrix, where N denotes a number of atoms in the molecular structure;

generating a binary adjacency matrix A for each chemical bond with elements $A_{i,j}$ indicating whether a node i and a node j are connected via a chemical bond;

propagating the atomic features at each layer of a graph-convolutional neural network (GCNN) according to the following:

$$X^{(l+1)} = \sigma\left(\tilde{D}^{-\frac{1}{2}} \tilde{A} \tilde{D}^{-\frac{1}{2}} X^{(l)} W^{(l)}\right),$$

where $$\tilde{A} = A + I, \ \tilde{D}_{ii} = \Sigma_j \tilde{A}_{ij} \text{ and } \tilde{D}_{ij} = 0$$

for $i \neq j$, I represents an identity matrix of the same size as A, l represents a convolutional layer in the GCNN, $X^{(l)}$ represents the atomic features at layer l, $W^{(l)}$ represents neural weights, and $\sigma(\cdot)$ is a nonlinear function used in the GCNN;

assigning a score $\hat{x}_n$ to each atom indicating its importance for predicting a given chemical characteristic y, wherein determined according to the following:

$$\hat{x}_n = \sum_{j=1}^{d_L} \omega_j X_{n,j}^{(L)} + \omega_0,$$

where $X^{(L)}$ is a feature matrix of size $N \times d_L$ and $w_j$ and $w_o$ are softmax classifier parameters;

generating a visual representation of the molecular structure based on the chemical representation, x̂n, and y;

identifying groups of atoms for the given chemical characteristic from the visual representation;

storing the identified groups of atoms for the given chemical characteristic in a database; and designing a new molecule having the given chemical characteristic based on the stored identified groups of atoms.

6. The method as set forth in claim 5, wherein the one or more processors further perform an operation of causing a molecule synthesizer to synthesize the new molecule.

7. The method as set forth in claim 5, wherein the one or more processors further perform an operation of predicting a chemical characteristic of an input molecular structure without a priori knowledge.

8. The method as set forth in claim 5, wherein the one or more processors further performs an operation of training the neural network to obtain parameters $W^{(l)}$, for l = 1, ..., L and $\omega_j$, for j = 0, ..., $d_L$, where L represents a total number of convolutional layers, where $\omega_j$ represents a softmax classifier parameter, and wherein a mean squared error loss function is minimized as follows:

$$argmin_{W^{(l)},\omega} \sum_k \left\| \frac{1}{N} \sum_{n=1}^{N} \underbrace{\left( \sum_{j=1}^{d_L} \omega_j \left( X^k \right)^{(L)}_{n,j} + \omega_0 \right)}_{\hat{x}_n} - y^k \right\|_2^2,$$

where $(X^k)^{(0)}$ represents atomic features from a k'th molecular structure in a training set, $d_L$ is a dimension of the atomic feature in the $L^{th}$ layer, $y^k$ is a ground-truth chemical characteristic, and $(X^k)^{(l+1)} = \sigma\left( \left( \tilde{D}^k \right)^{-\frac{1}{2}} \left( \tilde{A}^k \right) \left( \tilde{D}^k \right)^{-\frac{1}{2}} \left( X^k \right)^{(l)} W^{(l)} \right)$.

9. A computer program product automatically identifying chemical properties of a molecule, the computer program product comprising:
  computer-readable instructions stored on a non-transitory computer-readable medium that are executable by a computer having one or more processors for causing the processor to perform operations of:
    converting a chemical representation of a molecular structure into a graph, wherein each node of the graph represents an atom in the chemical representation, and each edge of the graph represents a chemical bond in the chemical representation;
    generating a d-dimensional atomic feature for each atom, resulting in a N × d matrix, where N denotes a number of atoms in the molecular structure;
    generating a binary adjacency matrix A for each chemical bond with elements $A_{i,j}$ indicating whether a node i and a node j are connected via a chemical bond;
    propagating the atomic features at each layer of a graph-convolutional neural network (GCNN) according to the following:

$$X^{(l+1)} = \sigma\left( \tilde{D}^{-\frac{1}{2}} \tilde{A} \tilde{D}^{-\frac{1}{2}} X^{(l)} W^{(l)} \right),$$

where $$\tilde{A} = A + I, \tilde{D}_{ii} = \Sigma_j \tilde{A}_{ij} \text{ and } \tilde{D}_{ij} = 0$$

for $i \neq j$, I represents an identity matrix of the same size as A, l represents a convolutional layer in the GCNN, $X^{(l)}$ represents the atomic features at layer l, $W^{(l)}$ represents neural weights, and $\sigma(\cdot)$ is a nonlinear function used in the GCNN;

assigning a score $\hat{x}_n$ to each atom indicating its importance for predicting a given chemical characteristic y, wherein $\hat{x}_n$ is determined according to the following:

$$\hat{x}_n = \sum_{j=1}^{d_L} \omega_j X_{n,j}^{(L)} + \omega_0,$$

where $X^{(L)}$ is a feature matrix of size N × $d_L$ and $w_j$ and $w_o$ are softmax classifier parameters;
  generating a visual representation of the molecular structure based on the chemical representation, $\hat{x}_n$, and y;
  identifying groups of atoms for the given chemical characteristic from the visual representation;
  storing the identified groups of atoms for the given chemical characteristic in a database; and
  designing a new molecule having the given chemical characteristic based on the stored identified groups of atoms.

10. The computer program product as set forth in claim 9, wherein the one or more processors further perform an operation of causing a molecule synthesizer to synthesize the new molecule.

11. The computer program product as set forth in claim 9, wherein the one or more processors further perform an operation of predicting a chemical characteristic of an input molecular structure without a priori knowledge.

12. The computer program product as set forth in claim 9, wherein the one or more processors further performs an operation of training the neural network to obtain parameters $W^{(l)}$, for l = 1, ..., L and $\omega_j$ for j = 0, ..., $d_L$, where L represents a total number of convolutional layers, where $\omega_j$ represents a softmax classifier parameter, and wherein a mean squared error loss function is minimized as follows:

$$argmin_{W^{(l)},\omega} \sum_k \left\| \frac{1}{N} \sum_{n=1}^{N} \underbrace{\left( \sum_{j=1}^{d_L} \omega_j \left( X^k \right)^{(L)}_{n,j} + \omega_0 \right)}_{\hat{x}_n} - y^k \right\|_2^2,$$

where $(X^k)^{(0)}$ represents atomic features from a k'th molecular structure in a training set, $d_L$ is a dimension of the atomic feature in the $L^{th}$ layer, $y^k$ is a ground-truth chemical characteristic, and $(X^k)^{(l+1)} = \sigma\left( \left( \tilde{D}^k \right)^{-\frac{1}{2}} \left( \tilde{A}^k \right) \left( \tilde{D}^k \right)^{-\frac{1}{2}} \left( X^k \right)^{(l)} W^{(l)} \right)$.

* * * * *